United States Patent
Morf et al.

(10) Patent No.: US 10,176,601 B2
(45) Date of Patent: Jan. 8, 2019

(54) METHODS AND SYSTEMS FOR IMPROVING IMAGE QUALITY OF PROJECTION IMAGE DATA ACQUIRED USING FLAT PANEL DETECTORS

(71) Applicant: VARIAN MEDICAL SYSTEMS INTERNATIONAL AG, Cham (CH)

(72) Inventors: Daniel Morf, Buch am irchel (CH); Viktor Steinlin, Otelfingen (CH)

(73) Assignee: VARIAN MEDICAL SYSTEMS INTERNATIONAL AG (CH)

(*) Notice: Subject to any disclaimer, the term of this patent is extended or adjusted under 35 U.S.C. 154(b) by 181 days.

(21) Appl. No.: 15/080,597

(22) Filed: Mar. 25, 2016

(65) Prior Publication Data

US 2017/0278277 A1    Sep. 28, 2017

(51) Int. Cl.
    *G06T 11/00*    (2006.01)
    *A61B 6/00*    (2006.01)
    *A61B 6/03*    (2006.01)
    *G01T 1/24*    (2006.01)

(52) U.S. Cl.
    CPC ............ *G06T 11/003* (2013.01); *A61B 6/032* (2013.01); *A61B 6/4085* (2013.01); *A61B 6/4233* (2013.01); *A61B 6/5205* (2013.01); *A61B 6/585* (2013.01); *G01T 1/247* (2013.01); *A61B 6/405* (2013.01); *A61B 6/482* (2013.01); *A61B 6/5252* (2013.01); *A61B 6/5282* (2013.01)

(58) Field of Classification Search
    CPC ......... G06T 11/003; G06T 2207/10081; A61B 6/4233; A61B 6/585; A61B 6/4291; A61B 6/032; A61B 6/4085; A61B 6/5205; A61B 6/482; A61B 6/5252; A61B 6/5282; G01T 7/005; G01T 1/2018; G01T 1/247; G01N 2223/419
    See application file for complete search history.

(56) References Cited

U.S. PATENT DOCUMENTS

| | | | | |
|---|---|---|---|---|
| 2011/0075908 A1* | 3/2011 | Kanagawa | ............. | A61B 6/025 382/131 |
| 2012/0275678 A1* | 11/2012 | Liu | ........................ | A61B 6/585 382/132 |
| 2014/0064458 A1* | 3/2014 | Jobst | ........................ | A61B 6/00 378/207 |

\* cited by examiner

*Primary Examiner* — Yon J Couso
(74) *Attorney, Agent, or Firm* — Su IP Consulting (57) ABSTRACT

One example method to improve image quality of projection image data may include obtaining projection image data and channel offset data associated with the projection image data. The channel offset data may be acquired using the flat panel detector and include at least one set of channel offset data values associated with respective channels of the flat panel detector. The method may also include generating channel offset drift data representing one or more variations of the channel offset data from a reference channel offset data. The method may further include generating offset-compensated projection image data by modifying the projection image data based on the channel offset drift data to compensate for the one or more variations of the channel offset data.

17 Claims, 9 Drawing Sheets

METHODS AND SYSTEMS FOR IMPROVING IMAGE QUALITY OF PROJECTION IMAGE DATA ACQUIRED USING FLAT PANEL DETECTORS

BACKGROUND

Unless otherwise indicated herein, the approaches described in this section are not prior art to the claims in this application and are not admitted to be prior art by inclusion in this section.

Computerized tomography (CT) involves the imaging of the internal structure of a target object by collecting projection image data in a single scan operation ("scan"). CT is widely used in the medical field to view the internal structure of selected portions of the human body. In an ideal imaging system, rays of radiation travel along respective straight-line transmission paths from the radiation source, through a target object, and then to respective pixel detectors of the imaging system to produce accurate projection image data and volume data (e.g., volumetric image) without artifacts.

However, in practice, projection image data may contain errors or inconsistencies that result in artifacts in volume data reconstructed from the projection image data. For example, projection image data acquired using a flat panel detector may be affected by physical characteristics of the flat panel detector, such as due to offset, gain, nonlinearity and lag, etc. All of the foregoing lead to image degradation and affects any subsequent processing or diagnosis and treatment planning. It is therefore desirable to develop techniques for improving image quality of the projection image data to reduce artifacts in the volume data.

SUMMARY

In at least one example of the present disclosure, there is disclosed a method to improve image quality of projection image data acquired using a flat panel detector having pixel elements arranged in rows and channels. The method may include obtaining projection image data that includes projection image data values associated with respective pixel elements of the flat panel detector and obtaining channel offset data associated with the projection image data. The channel offset data may be acquired using the flat panel detector and include at least one set of channel offset data values associated with respective channels of the flat panel detector. The method may also include generating channel offset drift data representing one or more variations of the channel offset data from a reference channel offset data. The method may further include generating offset-compensated projection image data by modifying the projection image data based on the channel offset drift data to compensate for the one or more variations of the channel offset data.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the drawings, can be arranged, substituted, combined, separated, and designed in a wide variety of different configurations, all of which are explicitly contemplated herein.

Figure 1:
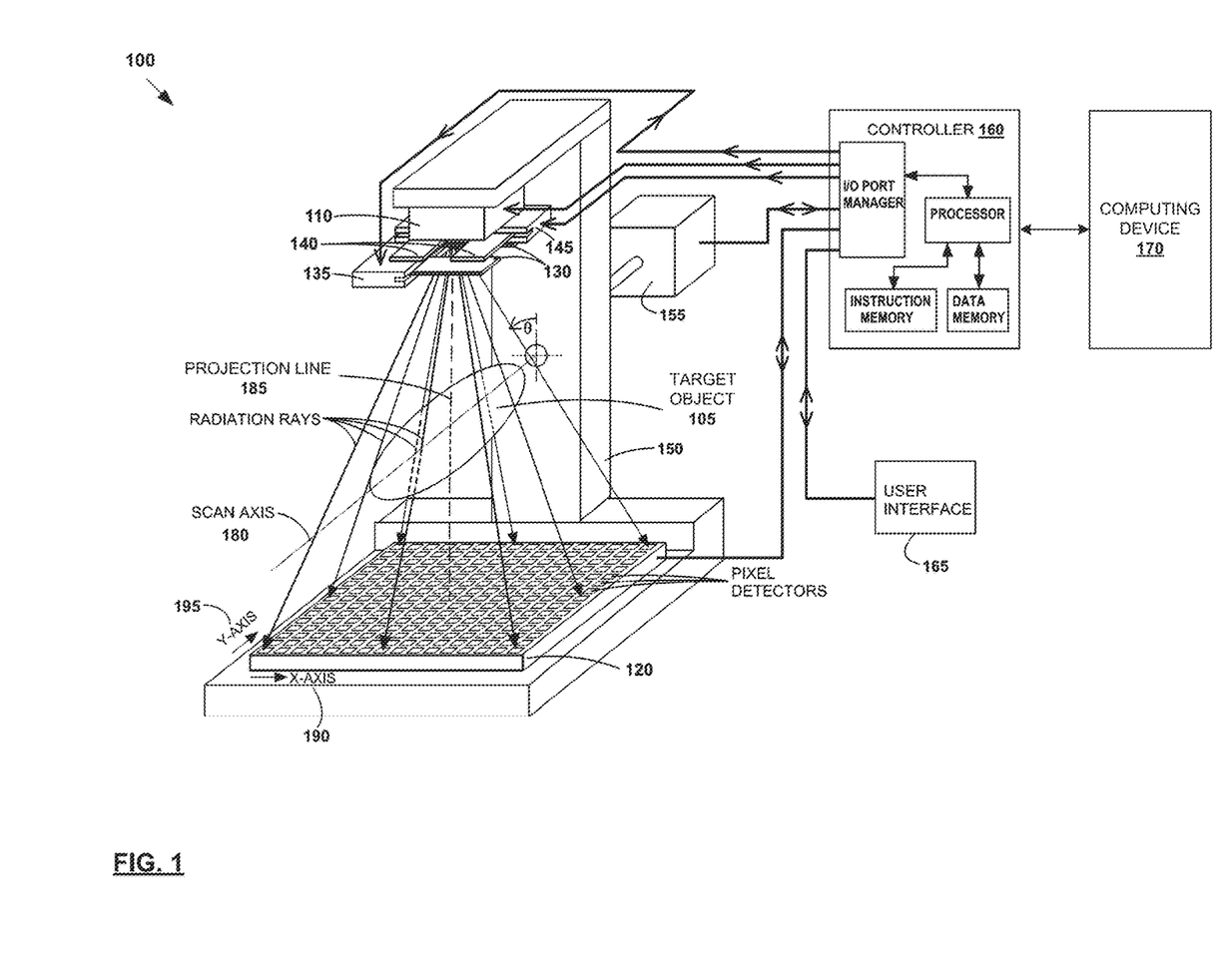
FIG. 1 is a schematic diagram illustrating an example imaging system.

FIG. 1 is a schematic diagram illustrating example imaging system 100. Although one example is shown, imaging system 100 may have alternative or additional components depending on the desired implementation in practice. In the example FIG. 1, imaging system 100 includes radiation source 110; detector 120 (e.g., flat panel detector to be discussed further using FIG. 2) having pixel detectors disposed opposite to radiation source 110 along a projection line (defined below; see 185); first set of fan blades 130 disposed between radiation source 110 and detector 120; and first fan-blade drive 135 that holds fan blades 130 and sets their positions. The edges of fan blades 130 may be oriented substantially perpendicular to scan axis 180, and are substantially parallel with trans-axial dimension 190 of detector 120.

Imaging system 100 also includes second set of fan blades 140 disposed between radiation source 110 and detector 120, and second fan-blade drive 145 that holds fan blades 140 and sets their positions. The edges of fan blades 140 may be oriented substantially parallel with scan axis 180, and are substantially perpendicular to axial dimension 195 of detector 120. Fan blades 130 and 140 are generally disposed closer to the radiation source 110 than detector 120. They are normally kept wide open to enable the full extent of detector 120 to be exposed to radiation, but may be partially closed in certain situations. Any additional or alternative beam-limiting device(s) may be used. For example, imaging system 100 may include a multileaf collimator having leafs (e.g., 120 leafs) that are individually controllable to adapt the beam shape to any desired form.

Gantry 150 of imaging system 100 holds at least radiation source 110, detector 120, and fan-blade drives 135 and 145 in fixed or known spatial relationships to one another. Mechanical drive 155 that rotates gantry 150 about target object 105 (e.g., patient) is disposed between radiation source 110 and detector 120, with target object 105 being disposed between fan blades 130 and 140 on the one hand, and detector 120 on the other hand. The term "gantry" has a broad meaning, and covers all configurations of one or more structural members that can hold the above-identified components in fixed or known (but possibly movable) spatial relationships. For the sake of visual simplicity in the figure, the gantry housing, gantry support, and fan-blade support are not shown.

Imaging system 100 further includes controller 160, user interface 165, and computing device 170. Controller 160 may be electrically coupled to radiation source 110, mechanical drive 155, fan-blade drives 135 and 145, detector 120, and user interface 165. User interface 165 may be configured to enable a user to initiate and configure a scan of target object 105, process projection image data acquired from detector 120, etc. User interface 165 may be configured to present graphic representations of the measured projection data. Computing device 170, coupled to controller 160, may be configured to perform simulation operations, data processing operations, and other operations that will be described in more detail below.

In imaging system 100, gantry 150 may be configured to rotate about target object 105 during a scan such that radiation source 110, fan blades 130 and 140, fan-blade drives 135 and 145, and detector 120 circle around target object 105. More specifically, gantry 150 may rotate these components about scan axis 180. As shown in FIG. 1, scan axis 180 intersects with projection line 185, and is typically perpendicular to projection line 185. Target object 105 is generally aligned in a substantially fixed relationship to scan axis 180. The construction provides a relative rotation between projection line 185 on one hand, and scan axis 180 and target object 105 aligned thereto on the other hand, with the relative rotation being measured by an angular displacement value θ.

Mechanical drive 155 may be coupled to the gantry 150 to provide rotation upon command by controller 160. The array of pixel detectors on detector 120 may be periodically read to acquire projection image data. Detector 120 has X-axis 190 and Y-axis 195, which are perpendicular to each other. Detector 120 may be oriented such that its Y-axis 195 is parallel to scan axis 180. For this reason, Y-axis 195 may also be referred to as the axial dimension of detector 120, and X-axis 190 may be referred to as the trans-axial dimension, or lateral dimension, of detector 120.

X-axis 190 is perpendicular to a plane defined by scan axis 180 and projection line 185, and Y-axis 195 is parallel to this same plane. A smaller number of pixels are shown in the figure for the sake of visual clarity. Detector 120 may be centered on projection line 185 to enable full-fan imaging of target object 105, may be offset from projection line 185 to enable half-fan imaging of target object 105, or may be movable with respect to projection line 185 to allow both full-fan and half-fan imaging of target object 105.

Throughout the present disclosure, the term "projection image data" may refer generally to one or more two-dimensional images that are acquired using any suitable two-dimensional acquisition approach, including X-ray computed tomography, radiography, fluoroscopy, etc. The term "projection image data" may be used interchangeably with "projection data", "projection(s)", "radiographic projection(s)" and "projection image(s)." The terms "projection view" and "projection angle" (i.e., angle at which projection image data is acquired) may be used interchangeably. After the image acquisition process, three-dimensional volume image data may be reconstructed from two-dimensional projection image data using any suitable reconstruction algorithms. In practice, the volume image data is not limited to three-dimensional, and may be reconstructed four-dimensional volume data, five-dimensional volume data, etc.

Flat Panel Detector

Figure 2:
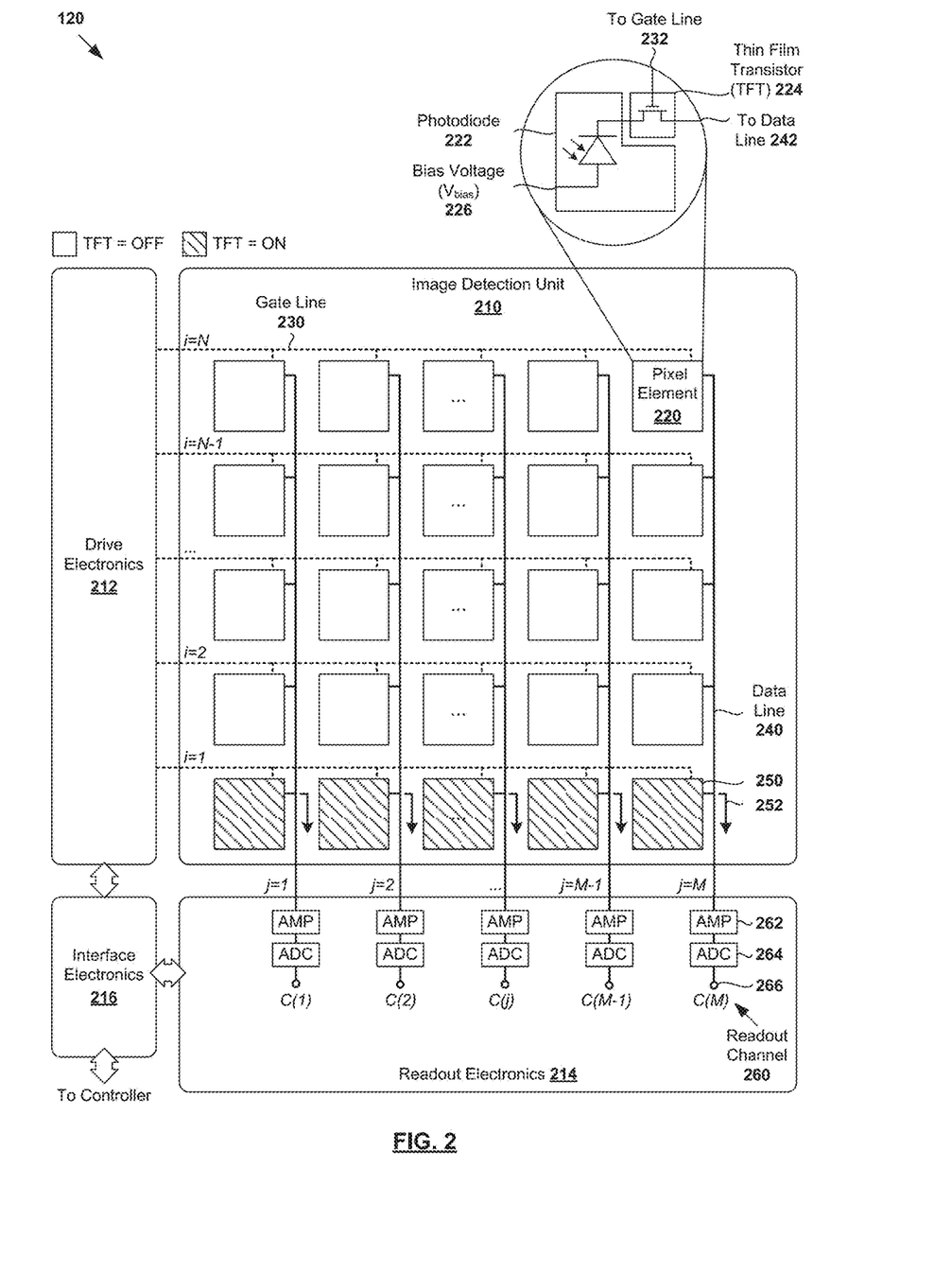
FIG. 2 is a schematic diagram illustrating an example flat panel detector.

According to one example, detector 120 is a flat panel detector (also known as "flat panel imager," "flat panel image detector," etc.). FIG. 2 is a schematic diagram illustrating example flat panel detector 120. In practice, flat panel imager 120 may have alternative or additional components than that shown in FIG. 2 depending on the desired implementation in practice. In this example, flat panel detector 120 includes image detection unit 210, drive electronics 212, readout electronics 214 and interface electronics 216.

Image detection unit 210 is configured to detect and convert X-ray photons to electrical signals using an array of pixel elements 220 (one labelled for simplicity) arranged in rows (e.g., along X-axis 190) and channels (also known as "columns"; e.g., along Y-axis 195). Coordinate (i, j) on an N×M array refers to pixel element 220 on row i and channel j, where i=1, . . . , N and j=1, . . . , M. In practice, any suitable number of rows (N) and channels (M) may be used. For example, image detection unit 210 may have a resolution of N×M=1024×768=786432 pixels, sensitive area=40×30 cm$^2$ and pixel pitch=0.392 mm. Pixel elements 220 on the same row i are connected to drive electronics 212 via gate line 230 (shown in dotted line; also known as "scan line" and "control line"). Pixel elements 220 on the same channel j are connected to readout electronics 214 via data line 240 (shown in bold line).

Also shown in more detail in FIG. 2, each array element 220 includes a photosensitive component in the form of amorphous silicon (a-Si) photodiode 222, and a switch component in the form of thin film transistor (TFT) 224. In practice, photodiodes 222 are deposited on a glass substrate with a high-sensitivity scintillator coating such as cesium iodide (CsI), etc. The scintillator coating converts X-ray photons to light photons, which are converted to electrical charges by photodiode 222. The amount of electrical charges stored in photodiode 222 is indicative of the number of light photons received by pixel element 220. The cathode of photodiode 222 is connected to a source of TFT 216, and its anode connected to a bias voltage ($V_{bias}$) 226 that is common to all pixel elements 220. Connection to the common bias voltage is not shown in FIG. 2 for simplicity. The gate (see 232) of TFT 224 is connected to drive electronics 212 via gate line 230 and the drain (see 242) of TFT 224 to readout electronics 214 via data line 240.

Drive electronics 212 and readout electronics 214 may be controlled via interface electronics 216 (e.g., using controller 160 and/or computing device 170 in FIG. 1). Drive electronics 212 is configured to enable readout from each row of pixel elements 220 of image detection unit 212. For example, when row i=1 is enabled (see 250), TFT 224 of each pixel element 220 on that row is switched ON to a conducting state to transfer electrical charges stored in photodiode 222 (see 252) to readout electronics 214. This allows electrical charges stored in pixel elements 220 on row i=1 to be transferred in parallel (i.e., channels 1, ..., M) to readout electronics 214 via respective data lines 240. The magnitude of the electrical charges are indicative of the intensity of X-ray photons delivered to image detection unit 210, and light photons detected by photodiodes 222.

Readout electronics 214 includes multiple readout channels 260 (one labelled for simplicity) for respective channels 1 to M. Each readout channel 260 includes channel charge amplifier 262 (labelled "AMP") and analog-to-digital converter (ADC) 264. In practice, readout electronics 214 may be implemented using an application-specific integrated circuit (ASIC) and known as digital readout ASIC (DRA), etc. Amplifier 262 is to amplify an electrical signal from a particular channel and ADC 264 is to convert the amplified electrical signal from analog to digital. In the example in FIG. 2, channel output 266 of corresponding readout channel 260 is represented as C(j) for j=1, ..., M. When read in parallel for a particular row i, channel outputs 266 form a one-dimensional "line" that includes a set of M values, i.e., C(1), C(2), ..., C(M).

The readout process is performed serially (i.e., row by row) until electrical charges from all rows are transferred from pixel elements 220 to readout electronics 214. During a readout cycle, channel outputs 266 from the first row (e.g., row=1) represent a first line or start of frame (SOF) of the acquired projection image data. Channel outputs 266 from the last row (e.g., row=N) represent a last line or end of frame (EOF) of the acquired projection image data. The readout cycle may be repeated to obtain multiple frames as gantry 150 and detector 120 are rotated about target object 105. The frames may then be used for subsequent processing and image reconstruction.

Although an example is shown in FIG. 2, it should be understood that any other suitable configuration(s) or component(s) may be used. For example, flat panel detector 120 may use a different readout scheme. The rows and channels in the array of pixel elements 220 may be swapped. Also, flat panel detector 120 may be partitioned into two or more partitions, in which case multiple partitions may be read out simultaneously. Also, although an indirect converter panel is exemplified in FIG. 2, a direct converter panel or any other suitable panel may be used.

In practice, projection image data acquired using flat panel detector 120 exhibits or causes unwanted artifacts that degrade image quality and/or image acquisition speed. For example, each channel output 266 may include an "offset" that is independent of the incident X-ray photons delivered to image detection unit 210. As used herein, the term "pixel offset" may refer generally to an offset associated with a particular pixel element 220. Pixel offset often varies from one pixel to pixel due to a number of factors, such as the so-called dark current, etc. The dark current flows in photodiode 222 and causes electrical charges to accumulate even in the absence of any X-ray irradiation on image detection unit 210. Pixel offset is generally corrected using standard compensation and calibration techniques that are performed offline, typically once a day or week and never during a scan.

As used herein, the term "channel offset" may refer generally to an offset associated with a particular readout channel 260. Channel offset varies from channel to channel due to the characteristics of readout electronics 214 and/or image detection unit 210. For example, the channel offset may "drift" or vary with temperature and/or time. Temperature differences or other changes in the ambient environment can cause offset variations in the conversion process of readout amplifier 262 and ADC 264 of each readout channel 260, etc. If these variations are too high, significant image artifacts can be observed. Channel offset generally cannot be corrected with conventional pixel offset compensation and other standard calibration techniques. Throughout the present disclosure, the term "channel offset drift" may refer generally to variations or changes in the channel offset.

Conventionally, to correct or compensate for the channel offset drifts, it is necessary to keep the temperature of flat panel detector 120 relatively stable or setting a long warm-up time until the temperature is stabilized. However, it is difficult to keep the temperature stable in practice, especially as flat panel detector 120 and gantry 150 are rotated about target object 105 during projection image data acquisition. Most of the heat is generated on one side of flat panel detector 120, which changes the heat profile of flat panel detector 120 significantly as it is rotated. In this case, it is not possible to get a very accurate readout before the heat profile of flat panel detector 120 stabilizes. Further, in some cases, it may take up to 30 minutes for the temperature to stabilize, if not longer. In addition to the temperature dependence, there might also be a dependence on time due to, for instance, reference or other signal fluctuation (e.g., 1/f noise).

According to examples of the present disclosure, image quality of projection image data acquired using flat panel detector 120 may be improved by performing one or more compensation methods. As will be discussed using FIG. 3, FIG. 4, FIG. 5, FIG. 6A to FIG. 6C, channel offset compensation will be described to compensate for variations in channel offset (i.e., channel offset drifts). Further, according to examples of the present disclosure, image quality may be improved using gain compensation (see FIG. 7), nonlinearity compensation (see FIG. 8) and lag compensation. In practice, the compensation methods may be implemented using flat panel detector 120, controller 160, computing device 170 of FIG. 1, dedicated circuitry (not shown for simplicity), any combination thereof or any other suitable component/circuitry. The compensation methods may be used together or independently.

Channel Offset Compensation

Figure 3:
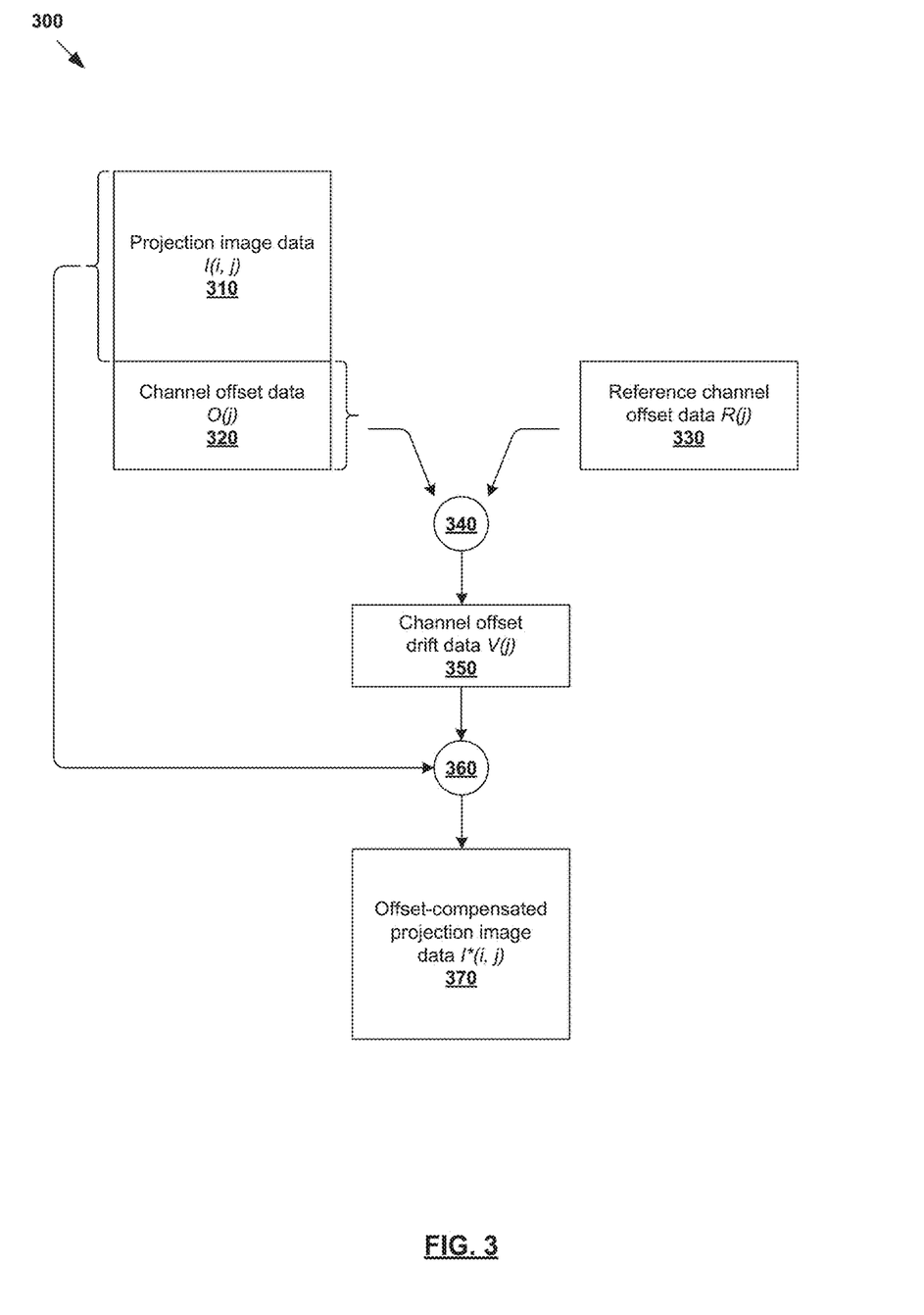
FIG. 3 is a flowchart of an example process to improve image quality of projection image data acquired using a flat panel detector by performing channel offset compensation.

FIG. 3 is a flowchart of example process 300 to improve image quality of projection image data acquired using flat panel detector 120 by performing channel offset compensation. Example process 300 may include one or more data types, operations, functions, or actions illustrated by one or more blocks, such as 310 to 360. The various blocks may be combined into fewer blocks, divided into additional blocks, and/or eliminated based upon the desired implementation. In contrast with conventional offset correction that uses offline algorithms, example process 300 may be performed online, as projection image is acquired during a scan. For example, if 900 projection images are acquired over different readout cycle, additional projection can be readout to determine the channel offset drift.

Referring to 310 in FIG. 3, projection image data 310 acquired using flat panel detector 120 is obtained. As used herein, the term "obtained" or "obtain" may refer to either receiving projection image data 310 (e.g., from controller 160 or detector 120) or retrieving it from a storage device. Projection image data 310 includes projection image data values I(i, j) associated with respective pixel elements 220 arranged in rows (i=1, ..., N) and channels (j=1, ..., M). As explained using FIG. 2, the projection image data values may be acquired from readout channels 260 serially from the first row (e.g., i=1) to the last row (e.g., i=N). For a particular row i=1, projection image data values I(i, 1), . . . , I(i, M) represents a one-dimensional "image line." Projection image data 310 represents real image information of target object 105 subject to X-ray irradiation and includes image lines from all rows.

Referring to 320 in FIG. 3, channel offset data 320 associated with projection image data 310 is obtained. Channel offset data 320 is acquired using flat panel detector 120 and includes channel offset data values O(1), . . . , O(M) associated with respective readout channels 260. Channel offset data 320 does not contain any real image information of target object 105, but rather channel offsets of respective readout channels 260 that can be used for channel offset compensation. Each set of channel offset data values O(1), . . . , O(M) represents a one-dimensional "dummy line." In practice, multiple dummy lines (i.e., multiple sets) may be acquired during a readout cycle, in which case a first dummy line may be represented as $O_1(1), \ldots, O_1(M)$, a second dummy line as $O_2(1), \ldots, O_2(M)$, and so on.

Example acquisition of projection image data 310 and channel offset data 320 will be described in further detail using FIG. 4 and FIG. 5. Flat panel detector 120 may be configured to perform the acquisition, usually indirectly by computing device 170 via controller 160. However, flat panel detector 120 may be configured by computing device 170 directly, or by any other suitable device, etc. Flat panel detector 120 may be configured to acquire channel offset data 320 (1) substantially immediately after projection image data 310 (e.g., after the last line or EOF of projection image data 310 is acquired), (2) substantially immediately before projection image data 310 (e.g., before the first line or SOF of projection image data 310 is acquired), (3) during acquisition of projection image data 310, etc. Here, the term "substantially immediately" may refer generally to a sufficiently small time difference to acquire channel offset data 320 that represents channel offsets affecting the quality of projection image data 310. Since the values of channel offset data 320 may vary, this improves the accuracy of subsequent channel compensation.

Referring to 330, 340 and 350 in FIG. 3, channel offset drift data 350 is generated based on one or more variations of channel offset data 320 from reference channel offset data 340. Reference channel offset data 340 includes reference channel offset data values R(1), . . . , R(M) associated with respective readout channels 260. Any suitable approach may be used to acquire reference channel offset data 340, such as by reading out a dedicated row of flat panel detector 120 that is not sensitive to light but has substantially the same properties as that of other rows. As discussed, variations of channel offset data 320 from reference channel offset data 340 may be caused by temperature of flat panel detector 120, its usage duration (time), or a combination of both.

Channel offset drift data 350 may include values V(1), . . . , V(M), where V(j) is calculated based on O(j) and R(j) for j=1, . . . , M. Any suitable approach may be used to generate channel offset drift data 350. In one example, a simple subtraction may be performed to calculate V(j)=O(j)−R(j), i.e., to generate V(j) based on variation(s) of O(j) from R(j). If there are multiple dummy lines (i.e., multiple sets of O(j)), one dummy line is selected or an average is calculated from multiple dummy lines before performing the subtraction. More advanced techniques may also be used. For example, using adaptive filtering, a higher filter gain may be applied after new image readout timings are loaded. This allows adjustment to the correction value faster. After a couple of image readouts, the gain may be lowered to reduce the noise associated with the readout. Hence, the filter parameter(s) are adapted to the number of image readouts since the last configuration change.

Referring to 360 and 370 in FIG. 3, offset-compensated projection image data I*(i, j) 370 is generated by performing channel offset compensation to modify projection image data 310 based on channel offset drift data 350. By compensating for variations of channel offset data 320 from reference channel offset data 340, offset-compensated projection image data 370 has improved image quality compared to projection image data 310, such as reduction in column artifacts (to be explained further using FIG. 6A to FIG. 6C).

In one example, each offset-compensated projection image data value may be calculated as I*(i, j)=I(i, j)−V(j), i.e., by subtracting the channel offset drift data value V(j) of the corresponding channel from projection image data value I(i, j). As an example, for a particular channel j=1, the corresponding offset-compensated projection image data values include I*(1, 1), I*(2, 1), . . . , I*(N, 1), where I*(i, 1)=I(i, 1)−V(1) for rows i=1, . . . , N. More advanced techniques may also be used, such as a polynomial fit of the last few channel offset drift values V(j) and using a predicted value for compensation, etc.

Examples of projection image data 310 and channel offset data 320 will now be described with reference to FIG. 4 and FIG. 5. In particular, FIG. 4 is a flowchart of example process 400 to acquire projection image data 310 and channel offset data 320 using flat panel detector 120 during a readout cycle. Example process 400 may include one or more data types, operations, functions, or actions illustrated by one or more blocks, such as 410 to 490. The various blocks may be combined into fewer blocks, divided into additional blocks, and/or eliminated based upon the desired implementation.

Figure 4:
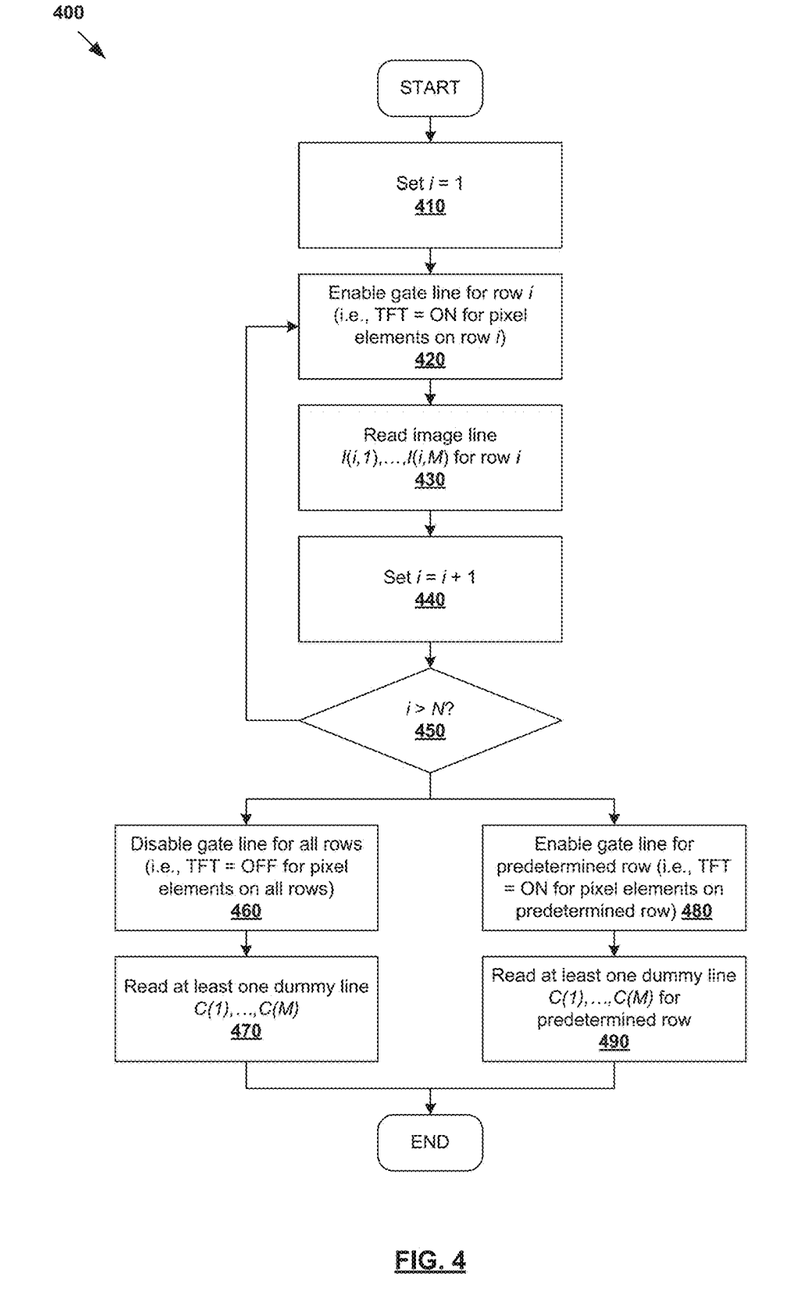
FIG. 4 is a flowchart of an example process to acquire projection image data and channel offset data using a flat panel detector during a readout cycle.

Referring first to 410 to 450 in FIG. 4, flat panel detector 120 is configured to acquire projection image data 310 from pixel elements 220 serially. In particular, at 410 and 420 in FIG. 4, a row counter or shift register(s) is initialized to first row i=1 and gate line 230 is enabled to perform readout from pixel elements 220 on that row. At 430 in FIG., TFT 224 of each pixel element 220 on row i=1 is switched on to transfer electrical charges from photodiode 222 to corresponding readout channel 260 via data line 240. As an example, for row i=1, channel outputs 266 represent one image line of projection image data 310 at I(1, 1), . . . , I(1, M).

At 440 in FIG. 4, the row counter is increased to select the next row i=2 for the readout. At 450 in FIG. 4, unless the last row i=N is reached, blocks 420 to 440 are repeated. The result is projection image data 310 that includes N×M projection image data values for respective pixel elements 220 of flat panel detector. In this example, the readout is performed from the first row i=1 to the last row i=N. In practice, however, any suitable order may be used.

Further, flat panel detector 120 is configured to acquire channel offset data 320 by performing blocks 460 and 470, or alternatively 480 and 490 in FIG. 4. Referring first to 460 and 470, channel offset data values O(1), . . . , O(M) may be acquired when all gate lines 230 for rows 1, . . . , N are disabled. In this case, at 460 in FIG. 4, TFT 224 of each and every pixel element 220 on flat panel detector 120 is switched off after projection image data 310 is acquired. Since TFT 224 is switched off, channel offset data 320 represents the readout channel offsets for respective readout channels 260, rather than image information from pixel elements 220 that is indicative of the incident X-ray photons delivered. One or more multiple dummy lines may be acquired during the same readout cycle by repeating 470.

Alternatively, referring to 480 and 490 in FIG. 4, channel offset data 320 may be acquired when gate line 230 is enabled for one or more predetermined rows, and disabled for all other rows. The predetermined row may be the first row (i.e., i=1), last row (i.e., i=N), or any row in between. Multiple predetermined rows may be used. In general, the offset error is one of the dominant errors. By reading the (dummy) predetermined row(s), the real signal is not read but all other parasitic signals that are readable during a normal readout will also be captured. As such, the difference between the measured signal of a normal cycle and the dummy row cycle should be the real signal. The examples are discussed below.

(1) In a first example, the predetermined row is the last row i=N. In this case, after the last line of projection image data 310 has acquired at 430 in FIG. 4, the same line is read again while keeping TFT 224 of associated pixel elements 220 switched on. The same line may be read multiple times to acquire multiple dummy lines. The advantage of this is that the channel offset data values O(1), . . . , O(M) represent offsets from a combination of image detection unit 210 and readout electronics 214 that may be subsequently compensated.

(2) In a second example, the predetermined row is the first row i=1. In this case, the first line is read out again while keeping TFT 224 of associated pixel elements 220 switched on. Similar to (1), multiple dummy lines may be acquired by reading the first line multiple times.

(3) In a third example, the predetermined row represents a dedicated compensation line that is read out when TFT 224 is on but pixel elements 220 associated with the compensation line are not sensitive to light. In addition to channel offsets associated with readout electronics 214, the channel offset data values O(1), . . . , O(M) for respective readout channels 260 represent potential offset drift of pixel elements 220 (photodiodes 222 and/or TFT 224) that may be subsequently compensated. Any suitable compensation line may be used. In one example, a particular row (e.g., last row i=N) may be covered such that no light can reach the pixels. The compensation line has substantially the same physical properties as other lines, but not sensitive to light. From a readout perspective, the compensation line is addressed and read out the same way as any other line.

FIG. 4 will be described with reference to FIG. 5, which is a timing chart illustrating multiple example readout cycles according to example process 400 in FIG. 4. Two example readout cycles labelled "A" (see 510) and "B" (see 520) are shown in FIG. 5. During each readout cycle 510/520, projection image data 310A/310B and channel offset data 320A/320B are acquired according to blocks 410 to 470 in FIG. 4. Frame trigger signal 530 is to trigger data acquisition; gate line control signal 540 is to control gate lines 230 (e.g., enabled to switch on TFT 224 or disabled to switch off TFT 224); and data line control signal 550 is to control data lines 240 during readouts. Channel output signal 550 represents values of projection image data 310A/310B or channel offset data 320A/320B acquired during readout cycle 510/520. Although not shown in FIG. 5, there might be any suitable time gap between readout cycles "A" (see 510) and "B" (see 520). For example, a readout cycle period might be 100 ms, while the time gap between two frame starts (e.g., between 512 and 522) may be 200 ms, or any time greater than the readout cycle period.

Referring to readout cycle "A" (see 510), first frame trigger 532 triggers the acquisition of projection image data 310A from the start of frame (see SOF 512) to the end of frame (see EOF 514). During the acquisition of projection image data 310A, gate line control signal 540 includes pulses that enable gate lines 230 serially to acquire the first image line from the first row (i=1) to the last image line from the last row (i=N). See also related 410 to 450 in FIG. 4.

Figure 5:
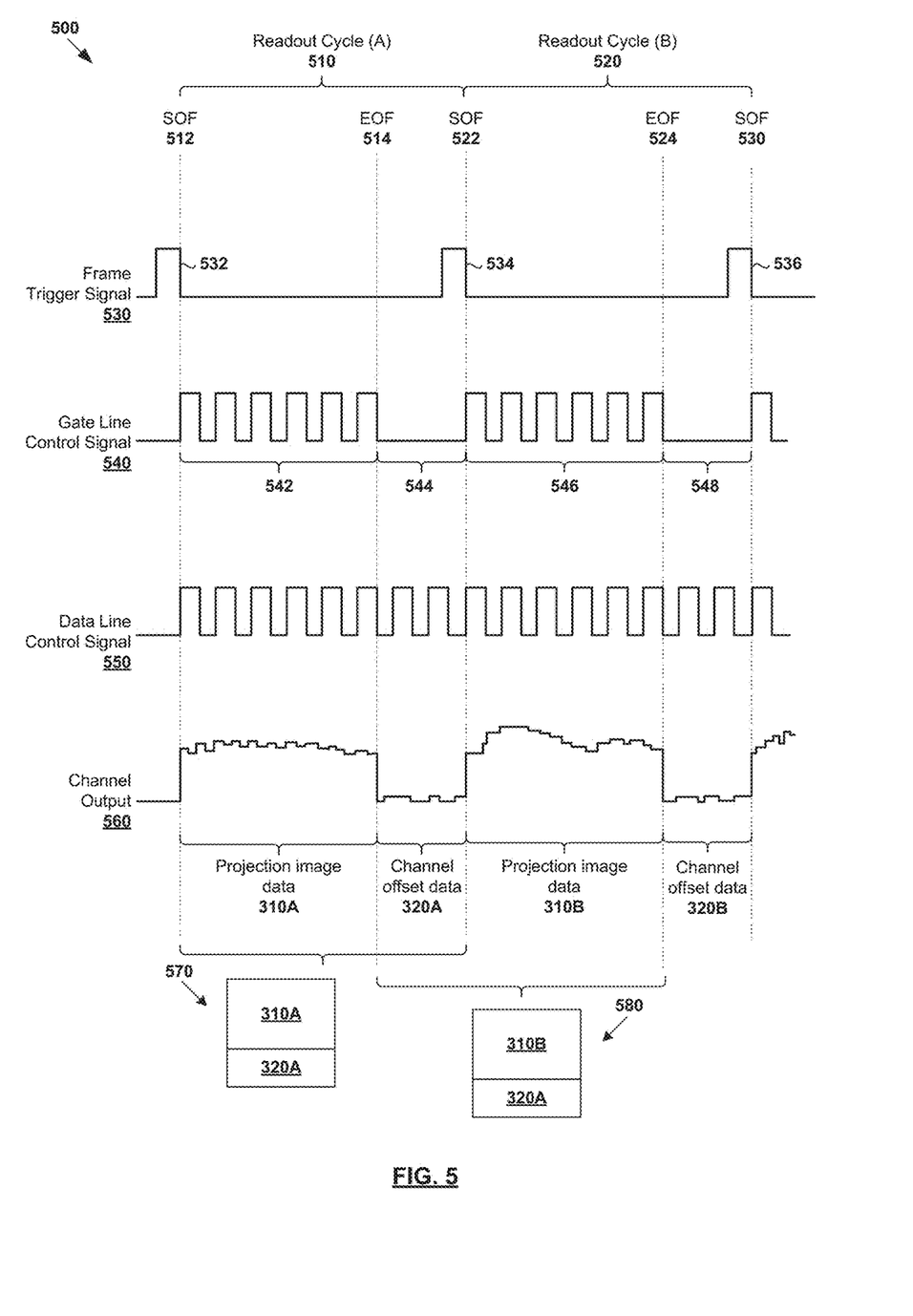
FIG. 5 is a timing chart illustrating multiple example readout cycles according to the example process in FIG. 4.

As shown at 544 in FIG. 5, there is generally some "dead time" after the last image line is acquired and before the next readout cycle "B" (see 520) is triggered by the next frame trigger 534. The dead time may be used to acquire channel offset data 320A while all gate lines 230 are disabled (i.e., all TFTs 224 switched off). To guarantee the best ADC conversion performance, data line control signal 550 may have a constant sampling rate during the dead time to read out multiple dummy lines according to 460 and 470 in FIG. 4.

The above is repeated during readout cycle B (see 520). Projection image data 310B is acquired when gate lines 230 are enabled serially (see 546) from the start of frame (see SOF 522) to the end of frame (see EOF 524). Channel offset data 320B is acquired during the dead time (see 548) after the last image line is acquired and when all gate lines 230 are disabled. Similarly, channel offset data 320B may include multiple dummy lines acquired according to related blocks 460 and 470 in FIG. 4.

The above channel offset data 320A/320B is acquired for channel offset compensation according example process 300 in FIG. 3. In one example, channel offset data 320A from readout cycle A (see 510) is used in channel offset compensation for projection image data 310A acquired in the same readout cycle. In other words, channel offset data 320A is acquired substantially immediately after projection image data 310A. In this case, as shown at 570 in FIG. 5, channel offset data 320A is appended to projection image data 310A at the end of the acquisition process.

Alternatively, channel offset data 320A acquired in readout cycle A (see 510) is used in channel offset compensation for projection image data 310B acquired in a different but adjacent readout cycle B (see 520). In other words, channel offset data 320A is acquired substantially immediately before projection image data 310B. As shown at 580 in FIG. 5, channel offset data 320A is appended to projection image data 310B from readout cycle B at the end of the acquisition process.

Any other suitable approach than that shown in FIG. 5 may also be used. For example, flat panel detector 120 may also be configured to acquire channel offset data 320 during the acquisition of projection image data 310. A temporal (or recursive) filter that averages dummy lines of multiple projection images may also be used. The averaged and weighted value may then be used in subsequent blocks.

Figure 6A:
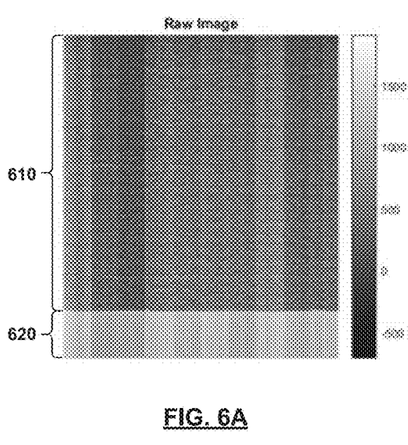
FIG. 6A illustrates example projection image data and channel offset data.
Figure 6B:
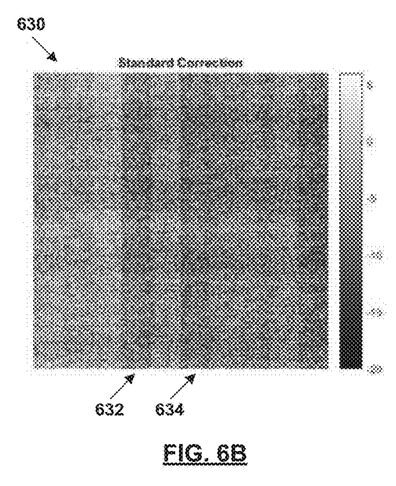
FIG. 6B illustrates projection image data generated using standard offset correction.

FIG. 6A, FIG. 6B, FIG. 6C and FIG. 6D illustrate example channel offset compensation according to the above examples. FIG. 6A illustrates example projection image data 610 and channel offset data 620. In this case, a dark field image (i.e., taken without any X-ray irradiation) is used as an example, but any flood field images may be used in practice. FIG. 6B illustrates projection image data 630 generated using standard offset correction. Such conventional techniques do not take into account variations in channel offsets.

Figure 6C:
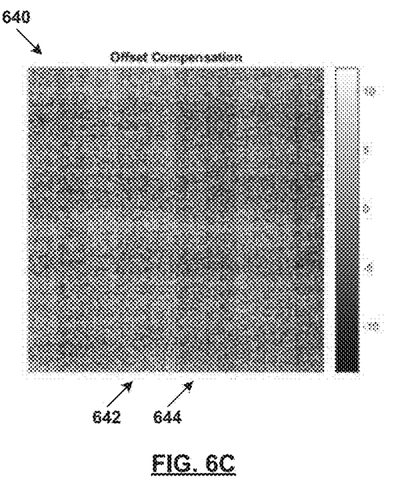
FIG. 6C illustrates offset-compensated projection image data generated using channel offset compensation according to the examples in FIG. 3, FIG. 4 and FIG. 5.
Figure 6D:
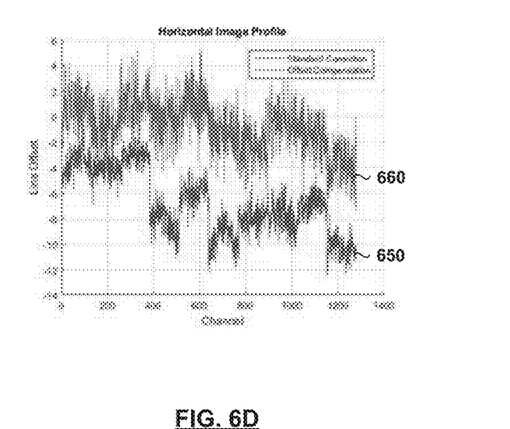
FIG. 6D illustrates horizontal image profiles of the projection image data in FIG. 6B and FIG. 6C.

FIG. 6C illustrates offset-compensated projection image data 640 generated using channel offset compensation according to the examples in FIG. 3, FIG. 4 and FIG. 5. Compared to FIG. 6B, channel-to-channel variations are reduced in FIG. 6C, such as at 642 (compared to 632) and at 644 (compared to 634). FIG. 6D illustrates horizontal image profiles 650, 660 of projection image data 630 with standard offset correction in FIG. 6B and offset-compensated projection image data 640 in FIG. 6C. Comparing the image profiles, variations in channel offset (Y-axis) are reduced among channels (X-axis) in image profile 660 of second example offset-compensated projection image data 640 in FIG. 6C compared to that of image profile 650.

Additional techniques may be used to further compensate for channel offset drifts. For example, a temperature-offset diagram may be used, such as a diagram that is specifically measured for flat panel detector 120, a predefined diagram, etc. The use of the predefined diagram is usually suitable if the temperature-offset diagram is relatively constant for most or all flat panel detectors 120. The temperature-offset diagram may be an N×M diagram with values for respective pixel elements 220 on flat panel detector 120. In one example, the temperature offset diagram may be a series of offset frames, where each offset frame is indicative of a specific temperature. During the correction, the temperature is measured and the appropriate offset frame is applied for correction (e.g., pixel by pixel correction). The correction may be performed in real time, or non-real-time. In another example, only the channel offsets are stored in the temperature-offset diagram. During readout, the offset value corresponding to the current temperature would be applied.

Further, tracking or filtering may be used to regulate the offset compensation filter such that after offset subtraction, the mean value of each channel offset will be equal to an arbitrary chosen offset ("nominal offset value"). In the example in FIG. 3, the tracking algorithm may be used to regulate channel offset drift data 350 such that data values $V(1), \ldots, V(M)$ for respective readout channels 260 will be substantially equal to a predetermined nominal offset value. In practice, channel offsets depend very much on the mode settings of the frame readout timing. For this reason, the tracking algorithm may be reset when switching between different modes. Any suitable filter may be used in practice, such as infinite impulse response (IIR), finite impulse response (FIR), etc.

In order to achieve a fast settling of an offset compensation filter, three complementary techniques may be applied. (1) In a first example, the compensation filter is initialized to values of a first dummy line acquired after mode switching. However, given the fact that a single line sample is affected by noise, the initially sampled values may be off by the amplitude of the pixel noise. (2) In a second example, the feedback filter coefficient is dynamically adapted. After mode switching, at the beginning of the settling phase, the feedback filter coefficient is higher and is then dynamically reduced after a certain number of frames. (3) In a third example, multiple dummy lines are sampled between each frame, such that the compensation filter is updated multiple times between each frame.

Gain Compensation

Besides channel offset compensation, image quality may be improved using gain compensation. In practice, the gain of pixel element 220 is generally a sum of the efficiency of the scintillation structure (including build up) of flat panel detector 120 and conversion efficiency of photodiode 222 and the electronics gain. As discussed using FIG. 2, the scintillation structure (e.g., cesium oxide) is a layer over pixel elements 220 that converts X-ray photons to light photons, which are in turn converted to electrical signals by photodiode 222. Due to radiation, however, it is possible that the efficiency of the scintillation structure as well as the efficiency of photodiode 222 is permanently changed. In this case, gain compensation is performed to homogenize different pixel and/or channel sensitivities.

Conventionally, gain compensation relies on frequent gain compensation, such as using gain maps. In some applications where regular gain calibrations can be performed, the change in efficiency may be compensated. However, this is not often possible in certain applications such as dosimetry because the calibration may be very time consuming and cannot be repeated often. For example, in dosimetric applications (e.g., absolute portal dosimetry), a pixel value is converted into a dose in water. If calibration changes or if some regions of an active area of flat panel detector 120 changes due to sensitivity loss, such changes will introduce errors in the dosimetric applications. As a result, the whole dosimetric measurement chain would have to be re-calibrated. When frequent gain map calibration cannot be performed, the pixel gain may only be factory-calibrated only, with no subsequent calibration in the field.

Figure 7:
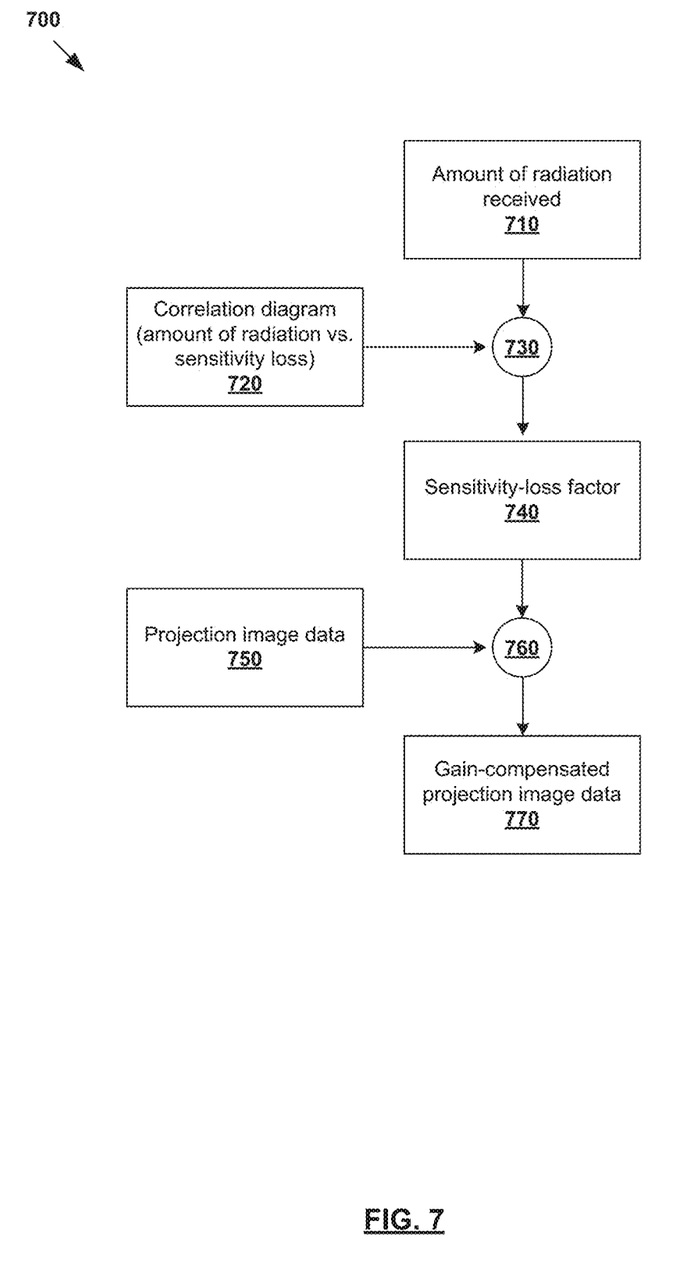
FIG. 7 is a flowchart of an example process to improve image quality of projection image data acquired using a flat panel detector by performing gain compensation.

According to examples of the present disclosure, gain compensation may be performed to take into account "sensitivity loss" (used interchangeably with "gain degradation" and "efficiency degradation") of flat panel detector 120 due to radiation. In more detail, FIG. 7 is a flowchart of example process 700 to improve image quality of projection image data acquired using flat panel detector 120 by performing gain compensation. Example process 700 may include one or more data types, operations, functions, or actions illustrated by one or more blocks, such as 710 to 770. The various blocks may be combined into fewer blocks, divided into additional blocks, and/or eliminated based upon the desired implementation.

Referring to 710 in FIG. 7, an amount of radiation received by flat panel detector 120 is determined. For example, dose maps may be recorded over the life time of flat panel detector 120 to calculate the amount of total radiation. Each dose map stores the amount of radiation received by each pixel element 220, for example, since flat panel detector 120 is first exposed to radiation.

Referring to 720, 730 and 740 in FIG. 7, sensitivity-loss correction factor 740 associated with the total amount of radiation is determined based on correlation diagram 720. For example, the determination operation at 730 may be based on a total radiation vs. sensitivity loss correlation diagram. In general, sensitivity degrades (i.e., higher sensitivity loss) as flat panel detector 120 is exposed to more radiation (i.e., higher amount of radiation received). Any suitable sensitivity-loss factor 740 may be used, such as N×M pixel-dependent values for respective pixel elements 220, etc. In some cases, a single value compensating a larger region (e.g., all pixel elements 220, readout channel 260, etc.) might be suitable depending upon the desired implementation. In practice, the correlation between the total amount of radiation and sensitivity loss is similar for flat panel detectors 120 of the same type and the same diagram may be used. For different panel types, different diagrams may be established.

Referring to 750, 760 and 770 in FIG. 7, gain compensation is performed by modifying projection image data 750 based on sensitivity-loss factor 740 to generate gain-compensated projection image data 770. The generation operation at 760 is to compensate for degradation caused by the amount of radiation to flat panel detector 120, and may involve applying sensitivity-loss factor 740 to projection image data values, $I(i, j)$, associated with pixel elements 220 arranged in rows $i=1, \ldots, N$ and channels $j=1, \ldots, M$. Since sensitivity-loss factor 740 changes based on the amount of total radiation received by flat panel detector 120, the required gain compensation will also change over time.

Example process 700 may be performed using computing device 170 of FIG. 1 and/or any other suitable device. It would be appreciated that gain compensation according to example process 700 in FIG. 7 may be performed after channel offset compensation according to example process 300 in FIG. 3. In this case, offset-compensated projection image data 310 in FIG. 3 is used as projection image data 750 in FIG. 7. Example process in 700 in FIG. 7 may also be performed independently of example process 300 in FIG. 3.

Channel Nonlinearity Compensation

Besides channel offset compensation and gain compensation, image quality may be improved using nonlinearity compensation. In practice, the linearity of each readout channel 260 could deviate from a straight line, mainly due to nonlinear behavior of readout electronics 214 (e.g., amplifiers 262 and/or ADCs 264). However, this nonlinear behavior may also be a result of the load (e.g., image detection unit 210) connected to readout electronics 214. Such nonlinear behavior could create visible image artifacts, especially when the nonlinearity varies from channel to channel.

Conventionally, it is generally not possible or very difficult to calibrate for nonlinearity. As a workaround, it is necessary to calibrate flat panel detector 120 at about the same signal level as the projection image data acquired. Although this may reduce the effect of nonlinearity, the dynamic range for such approach is limited.

Figure 8:
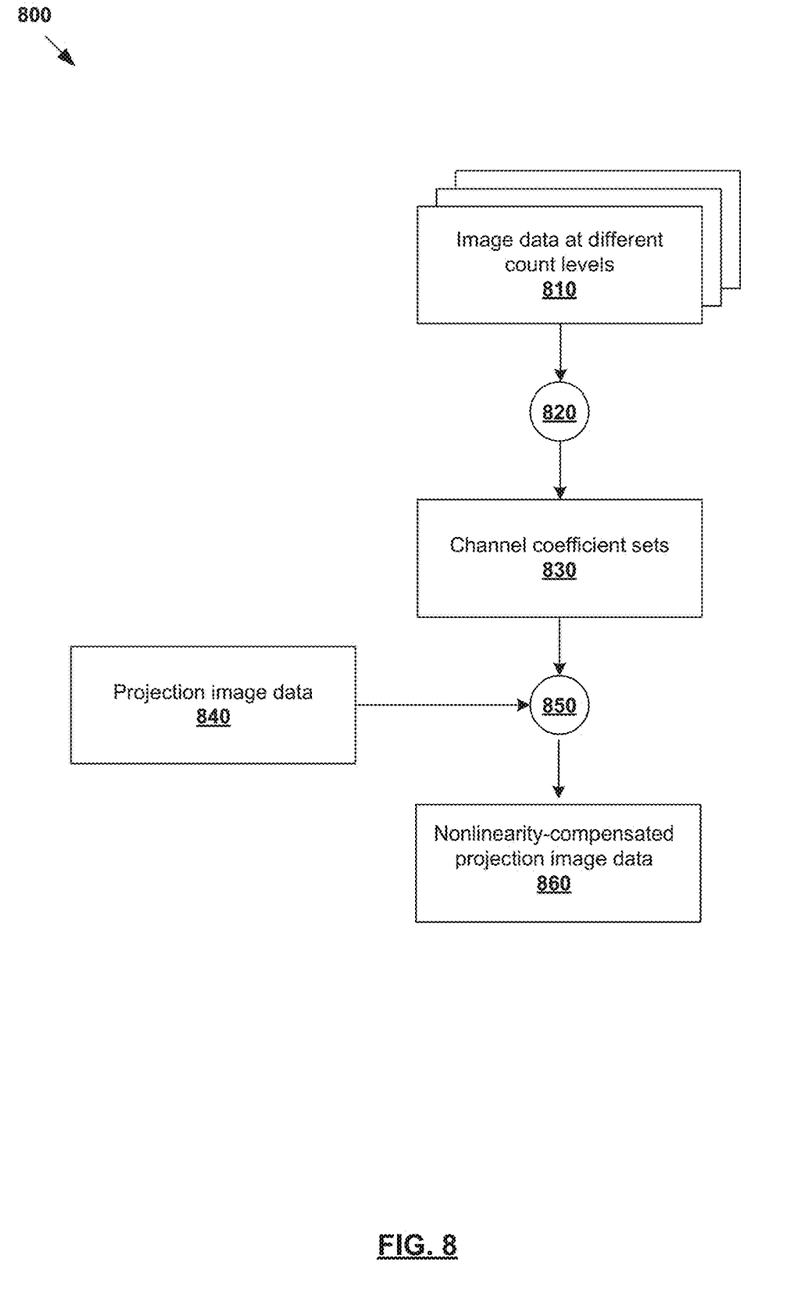
FIG. 8 is a flowchart of an example process to improve image quality of projection image data acquired using a flat panel detector by performing nonlinearity compensation.

According to examples of the present disclosure, nonlinearity compensation may be performed. In more detail, FIG. 8 is a flowchart of example process 800 to improve image quality of projection image data acquired using flat panel detector 120 by performing nonlinearity compensation. Example process 800 may include one or more data types, operations, functions, or actions illustrated by one or more blocks, such as 810 to 860. The various blocks may be combined into fewer blocks, divided into additional blocks, and/or eliminated based upon the desired implementation.

Referring to 810, 820 and 830 in FIG. 8, projection image data 810 is acquired at different levels of X-ray irradiation (e.g., based on count levels, intensity levels, etc.) to determine channel coefficient sets 830. For example, determination operation at 820 may involve fitting the different levels of projection image data 810 to a correction curve (e.g., polynomial curve) in order to calculate channel coefficient sets 830 for respective readout channels 266 for channels j=1, . . . , M (see FIG. 2), but not for every pixel element 220. Each channel coefficient set 830 may include one of more channel coefficient values. Also, the type of correction curve selected depends on which will fit projection image data 810 best. For the polynomial curve, for example, a grade or order of the polynomial is also selected. The correction curve may be pixel-dependent or channel-dependent. For example, for a $5^{th}$ order polynomial curve, channel coefficient set 830 includes five coefficient values.

Each channel coefficient set 830 derived from the correction curve may be used to indicate a response of the associated readout channel 260 to the different levels of X-ray irradiation. For a particular readout channel 260, the response may be nonlinear due to the behavior of readout electronics 214 of that readout channel 260. The response may also vary from one readout channel 260 to another. Since typical nonlinearity comes from readout electronics 214, one curve per channel might be sufficient. In practice, however, the same approach may be applied on a per-pixel basis.

Referring to 840, 850 and 860 in FIG. 8, projection image data 840 is modified based on channel coefficient sets 830 to generate nonlinearity-compensated projection image data 860. This allows compensation of any nonlinearity in the response of respective readout channels 260 due to nonlinearity of readout electronics 214.

In practice, the nonlinear behavior generally does not change over the lifetime of flat panel detector 120, in which case the channel coefficient sets 830 may be calculated once. However, if any components of the readout circuits are replaced, the compensation process should be repeated. The readout pixel value will be corrected with the polynomial curve fitting in addition to the standard linear gain correction.

Example process 800 may be performed using computing device 170 of FIG. 1 and/or any other suitable device. It would be appreciated that nonlinearity compensation according to example process 800 in FIG. 8 may be performed before or after channel offset compensation according to example process 300 in FIG. 3 and gain compensation according to example process 700 in FIG. 7. Example process 800 may also be implemented independently from channel offset and gain compensation.

Lag Compensation

Due to the nature of aSi photodiode 222, flat panel detector 120 may have some limitations in terms of lag. Here, the term "lag" may refer to any unwanted image signal that is still present in flat panel detector 120 after the first readout, for example due to the retention of electrical charges or signals in photodiode 222 from frame to frame or the afterglow of the scintillator. To reduce errors caused by lag, the following techniques may be used, such as when acquiring projection image data 310/310A/310B in FIG. 3 and FIG. 4, etc.

In a first example, a special readout technique that alternates between "dark field" and "flood field" may be employed during image acquisition using flat panel detector 120. Dark field acquisition refers generally to image acquisition from readout channels 260 without any X-ray irradiation, and the frame(s) acquired may be referred to as dark field image(s). On the other hand, flood field acquisition is performed with X-ray irradiation (i.e., with beam delivery) to acquire one or more flood field images. As used herein, the term "dark field image data" is used herein to refer generally to one or more dark field images, and the term "flood field image data" to one or more flood field images. To compensate for lag in pixel elements 220, the dark field image data may be used to modify (e.g., using subtraction) the flood field image data to generate lag-compensated image data.

In one example, a pre-pulse frame is read out using dark field acquisition. The pre-pulse frame (i.e., a dark field image) contains lag data of pixel elements and is used to compensate for lag in a subsequent flood field image data acquired using flood field acquisition. The flood field image data is assumed to include content that cannot be cleared out by previous frame readouts, and subtracting the pre-pulse frame from the flood field image data results in a lag-compensated image frame. Alternatively, in a second example, multiple dark field frames are read out in between two flood field frames in order to clear the lag of flat panel detector 120 that cannot be cleared by a single readout.

Mega Voltage Cone Beam Computed Tomography (MV CBCT)

In one example, imaging system 100 may be based on MV CBCT using a detector (e.g., flat panel detector 120) and linear accelerator (linac) that are adapted for MV imaging.

Compared to kilo Voltage (kV) CBCT, MV CBCT uses higher x-ray energy to acquire projection image data and provides advantages such as robustness to metal artifacts that can occur at kV energies when metal objects (e.g., fiducial markers, surgical clips, etc.) are present in the imaged volume.

Despite the above advantages, existing techniques for MV CBCT have various limitations, including considerably high dose, poor image quality and reduced Field-Of-View (FOV). According to examples of the present disclosure, enhanced MV CBCT techniques may be used to addressing at least one of the above limitations, improving quality while reducing dose. For example, items (1), (2), (3). (8), (9), (12) and (13) below relate to hardware configuration during image acquisition, and other items during image reconstruction.

(1) In a first example, FOV may be increased through repositioning of the detector of the MV CBCT imaging system. In particular, by moving the detector laterally to an off-centered position, the reconstruction diameter may be increased from 25 to 40 cm. For example, in existing portal imaging, detectors that are 40 cm wide and a full-fan acquisition with a source-to-detector (SDD) distance of 150 cm allow a reconstruction diameter of 25 cm. By moving the detector laterally to a current limit of linac collimation (e.g., 40×40 cm at isocenter), the reconstruction diameter is expanded to approximately 40 cm using the same detector size and SDD. With this technique, the gantry rotates 360 degrees during acquisition to achieve data completion for reconstruction. The configuration may also be adapted according to future changes to linac collimation. For example, the reconstruction diameter is currently mostly limited by the linac collimation, but may also depend on detector lateral motion and detector size.

(2) A bowtie filter may be used for MV CBCT in order to improve or optimize beam delivery to the patient anatomy. The bowtie filter may be configured to deliver lower dose to regions with low attenuation, and higher dose to regions with high attenuation.

(3) Accelerator output modulation may be used to decrease imaging dose. For example, the accelerator output may be modulated depending on the gantry position and patient orientation in order to account for the patient thickness. With prior knowledge on the patient anatomy, dose may be spared in the regions of the arc where the patient is thinner, such as in the case in anterior-posterior angles.

(4) Image quality may be improved through analytical spectrum correction. Image uniformity, which is the ability to obtain a flat representation of a uniform tissue, can be achieved by correct modeling of the beam hardening through the different traversed objects, especially a flattening filter. When projected in the detector, each ray crosses a different material length and composition. The flattening filter is an example, as each detector pixel sees a different flattening filer thickness. Modeling of these geometry parameters and physical attenuation properties of the filters and patient tissue allows a more precise estimation of the beam hardening process each ray is subjected to. This in turn enables a more accurate equalization of the counts in the detector. This approach requires the spectrum before the flattening filter (which is known) as an input.

(5) A reference dose chamber may be used for correcting dose fluctuations. In this case, each projection is produced with a slightly different beam flux. Correcting these output fluctuations allows a precise estimation of the tissue attenuation. In this approach, the accelerator's reference dose chamber reading is written to each acquired projection. During reconstruction, the ratio between the air norm dose chamber value and the projection dose chamber value is taken into account during a normalization step, yielding an MV projection corrected for the dose used. The internal dose measuring device or a separately mounted dose chamber can serve as a measurement device.

(6) Noise reduction may be performed through optimization of reconstruction filters. In one example, reconstruction filters may be adapted by taking into account the MV beam focal spot geometry and MV detector's spread function.

(7) MV projections may be used in reconstruction in combination with kV projections in a sequential or alternating fashion in order to obtain the attenuation information, which is complementary, from both energy ranges. The benefit of using both kV and MV is not restricted to dual energy (spectral imaging). Scatter and beam hardening corrections may also benefit from both acquisition principles.

(8) Dual scan CBCT with couch shift may also be used. In particular, the longitudinal range of the scan (Z-range) does not have to be limited by the cone angle or detector size in the Z-direction. Instead, the couch can be shifted and more projections acquired in a new circle to produce a single extended CBCT.

(9) Gating systems may be used in combination with the MV acquisition system in order to trigger image acquisition at desired moments, such as preferred respiratory phases, in order to reduce artifacts produced by respiratory motion.

(10) Scanning and reconstructing in a Tomosynthesis fashion may also be used. MV projections may be reconstructed in short arcs, as a complete coverage (180 degrees) is not an unavoidable requirement.

(11) Iterative reconstruction techniques may be used for noise reduction on MV CBCT reconstructions.

(12) Using advanced beam shaping, various beam energies and flattening filters combinations may be used to exploit the flexibility brought up by the analytical spectrum correction, including a flattening filter free option.

(13) Image acquisition may be triggered by any axis, such as time, dose, or any mechanical axis, etc.

Computing Device

Figure 9:
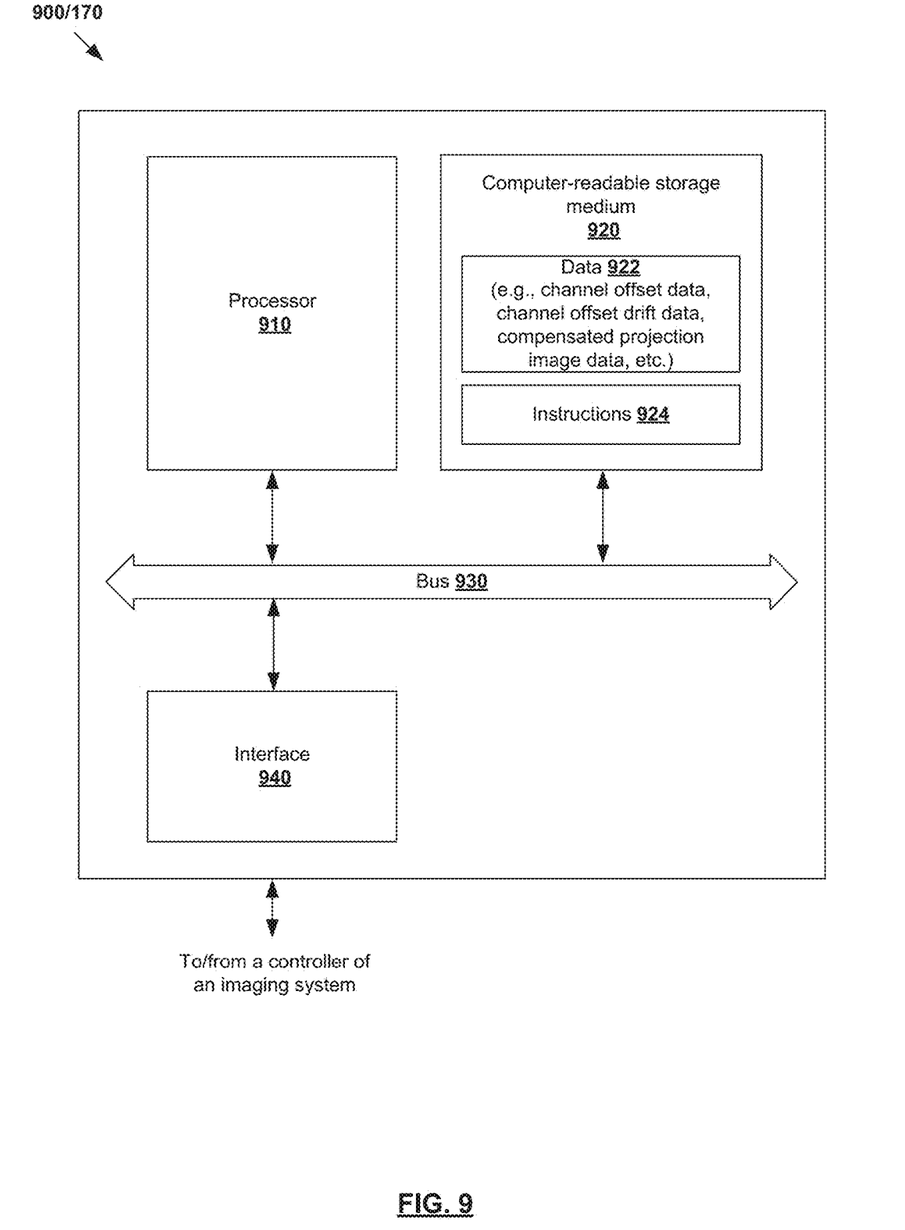
FIG. 9 is an example computing device configured to improve image quality of projection image data acquired using a flat panel detector.

The above examples can be implemented by hardware, software or firmware or a combination thereof. FIG. 9 is a schematic diagram of an example computing device 900/170 to improve image quality of projection image data acquired using flat panel detector 120. Example computing device 900/170 may include processor 910, computer-readable storage medium 920, interface 940 to interface with controller 160 of imaging system 100, and bus 930 that facilitates communication among these illustrated components and other components. Processor 910 is to perform processes described herein with reference to FIG. 1 to FIG. 8.

Computer-readable storage medium 920 may store any suitable data 922. For example, referring to FIG. 3, data 922 may include projection image data 310, channel offset data 320, reference channel offset data 330, channel offset drift data 350, offset-compensated projection image data 370, etc. Referring to FIG. 7, data 922 may include data relating to total radiation received 710, correlation diagram 720, sensitivity-loss factor 740, projection image data 750 and gain-compensated projection image data 770, etc. Referring to FIG. 8, data 922 may further include data relating to projection image data 810/840, channel coefficient sets 830, nonlinearity-compensated projection image data 860, etc. Computer-readable storage medium 920 may further store computer-readable instructions 924 which, in response to execution by processor 910, cause processor 910 to perform processes described herein with reference to FIG. 1 to FIG. 8.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

We claim:

1. A method to improve image quality of projection image data acquired using a flat panel detector having pixel elements arranged in rows and channels and a readout electronics, wherein each of the pixel elements includes a photosensitive component to store electrical charges and a switch component that is switched on to read out the electrical charges, the method comprising:
    obtaining projection image data that includes projection image data values associated with respective pixel elements of the flat panel detector;
    obtaining channel offset data associated with the projection image data and readout channels in the readout electronics, wherein the channel offset data is acquired by configuring the flat panel detector to switch off the switch component of each of the pixel elements or configuring the flat panel detector to switch on the switch component of each pixel element on one or more predetermined rows of the flat panel detector, and wherein the channel offset data includes at least one set of channel offset data values associated with respective channels of the flat panel detector;
    generating channel offset drift data representing one or more variations of the channel offset data from a reference channel offset data; and
    generating offset-compensated projection image data by modifying the projection image data based on the channel offset drift data to compensate for the one or more variations of the channel offset data.

2. The method of claim 1, wherein the predetermined row is one of the following: a last row of pixel elements from which projection image data values are acquired, a first row of pixel elements from which projection image data values are acquired, and a row of pixel elements that is not sensitive to light.

3. The method of claim 1, wherein the obtaining of the channel offset data comprises:
    configuring the flat panel detector to acquire the channel offset data substantially immediately before, during or substantially immediately after acquisition of the projection image data.

4. The method of claim 1, wherein the channel offset data includes multiple sets of channel offset data values and generating the channel offset drift data comprises:
    generating the channel offset drift data based on one or more variations of one of the multiple sets or an average of the multiple sets from the reference channel offset data.

5. The method of claim 1, wherein the method further comprises:
    performing tracking or filtering to regulate the channel offset drift data as the channel offset data and channel offset drift data change due to temperature, time, or a combination of both.

6. The method of claim 1, wherein the method further comprises:
    determining a sensitivity-loss factor based on an amount of radiation received by the flat panel detector; and
    generating gain-compensated projection image data by modifying the projection image data or offset-compensated projection image data based on the sensitivity-loss factor to compensate for degradation caused by the amount of radiation.

7. The method of claim 1, wherein the method further comprises:
    determining channel coefficient sets associated with respective channels of the flat panel detector, wherein each channel coefficient set includes one or more channel coefficients indicative of a response of the associated channel to different levels of X-ray irradiation; and
    generating nonlinearity-compensated projection image data by modifying the projection image data or offset-compensated projection image data based on the channel coefficient sets to compensate for a nonlinearity in the response of the respective channels.

8. The method of claim 1, wherein the obtaining of the projection image data comprises:
    performing dark field acquisition to acquire dark field image data and flood field acquisition to acquire the projection image data, wherein the dark field image data contains lag data of the pixel elements of the flat panel detector and the projection image data is acquired before or after the dark field image data; and
    correcting the projection image data by modifying the projection image data based on the dark field image data to compensate for the lag data of the pixel elements.

9. An imaging system configured to improve image quality of projection image data, comprising:
    a radiation source;
    a flat panel detector having pixel elements arranged in rows and channels and a readout electronics, wherein each of the pixel elements includes a photosensitive component to store electrical charges and a switch component that is switched on to read out the electrical charges;
    a controller; and
    a computing device coupled to the controller, wherein the computing device is configured to:
        obtain projection image data acquired using the flat panel detector that includes projection image data values associated with respective pixel elements of the flat panel detector;
        obtain channel offset data associated with the projection image data and readout channels in the readout electronics, wherein the channel offset data is acquired by configuring the flat panel detector to switch off the switch component of each of the pixel elements or configuring the flat panel detector to switch on the switch component of each pixel element on one or more predetermined rows of the flat panel detector, and wherein the channel offset data includes at least one set of channel offset data values associated with respective channels of the flat panel detector;

generate channel offset drift data representing one or more variations of the channel offset data from a reference channel offset data; and generate offset-compensated projection image data by modifying the projection image data based on the channel offset drift data to compensate for the one or more variations of the channel offset data.

10. The imaging system of claim 9, wherein the predetermined row is one of the following: a last row of pixel elements from which projection image data values are acquired, a first row of pixel elements from which projection image data values are acquired, and a row of pixel elements that is not sensitive to light.

11. The imaging system of claim 9, wherein the computing device is configured to obtain the channel offset data by performing the following:

configuring the flat panel detector to acquire the channel offset data substantially immediately before, during or substantially immediately after the acquisition of projection image data.

12. The imaging system of claim 9, wherein the channel offset data includes multiple sets of channel offset data values and the computing device is configured to generate the channel offset drift data by performing the following:

generate the channel offset drift data based on one or more variations of one of the multiple sets or an average of the multiple sets from the reference channel offset data.

13. The imaging system of claim 9, wherein the computing device is further configured to:

perform tracking or filtering to regulate the channel offset drift data as the channel offset data and channel offset drift data change due to temperature, time, or a combination of both.

14. The imaging system of claim 9, wherein the computing device is further configured to:

determine a sensitivity-loss factor based on an amount of radiation received by the flat panel detector; and generate gain-compensated projection image data by modifying the projection image data or offset-compensated projection image data based on the sensitivity-loss factor to compensate for degradation caused by the amount of radiation.

15. The imaging system of claim 9, wherein the computing device is configured to:

determine channel coefficient sets associated with respective channels of the flat panel detector, wherein each channel coefficient set includes one or more channel coefficients indicative of a response of the associated channel to different levels of X-ray irradiation; and generate nonlinearity-compensated projection image data by modifying the projection image data or offset-compensated projection image data based on the channel coefficient sets to compensate for a nonlinearity in the response of the respective channels.

16. The imaging system of claim 9, wherein the computing device is configured to configure the flat panel detector to acquire the projection image data by performing the following:

perform dark field acquisition to acquire dark field image data and flood field acquisition to acquire the projection image data, wherein the dark field image data contains lag data of the pixel elements of the flat panel detector and the projection image data is acquired before or after the dark field image data; and correct the projection image data by modify the projection image data based on the dark field image data to compensate for the lag data of the pixel elements.

17. A non-transitory computer-readable storage medium that includes a set of instructions which, in response to execution by a processor of a computing device, cause the processor to perform a method to improve image quality of projection image data acquired using a flat panel detector having pixel elements arranged in rows and channel and a readout electronics, wherein each of the pixel elements includes a photosensitive component to store electrical charges and a switch component that is switched on to read out the electrical charges, the method comprising:

obtaining projection image data that includes projection image data values associated with respective pixel elements of the flat panel detector;

obtaining channel offset data associated with the projection image data and readout channels in the readout electronics, wherein the channel offset data is acquired by configuring the flat panel detector to switch off the switch component of each of the pixel elements or configuring the flat panel detector to switch on the switch component of each pixel element on one or more predetermined rows of the flat panel detector, and wherein the channel offset data includes at least one set of channel offset data values associated with respective channels of the flat panel detector;

generating channel offset drift data representing one or more variations of the channel offset data from a reference channel offset data; and generating offset-compensated projection image data by modifying the projection image data based on the channel offset drift data to compensate for the one or more variations of the channel offset data.

* * * * *